United States Patent [19]

Slamon et al.

[11] Patent Number: 4,968,603

[45] Date of Patent: Nov. 6, 1990

[54] DETERMINATION OF STATUS IN NEOPLASTIC DISEASE

[75] Inventors: Dennis J. Slamon, Woodland Hills, Calif.; William L. McGuire, San Antonio, Tex.

[73] Assignee: The Regents of the University of California, Berkeley, Calif.

[21] Appl. No.: 948,265

[22] Filed: Dec. 31, 1986

[51] Int. Cl.$^5$ .................... C12Q 1/68; G01N 53/00; G01N 33/00

[52] U.S. Cl. .................... 435/6; 435/7; 935/77; 935/78; 436/501; 436/94

[58] Field of Search ............... 435/6, 7; 935/77, 78; 436/501, 94

[56] References Cited

U.S. PATENT DOCUMENTS

| | | | |
|---|---|---|---|
| 4,442,203 | 4/1984 | Varshausky | 435/6 |
| 4,490,472 | 12/1984 | Gottlieb | 435/6 |
| 4,535,058 | 8/1985 | Weinberg et al. | 435/6 |
| 4,665,018 | 5/1987 | Vold | 435/6 |
| 4,699,877 | 10/1987 | Cling et al. | 435/6 |
| 4,798,787 | 1/1989 | McCormick et al. | 435/7 |

OTHER PUBLICATIONS

Slamon et al., Science 224:256-264 (1984).
Semba et al. (1985), Proc. Natl. Acad. Sci., U.S.A. 82:6497-6501.
Coussens et al. (1985), Science 230:11321139.
King et al. (1985), Science 229:974-976.
Schechter et al. (1985), Science 229:976-978.
Fukushige et al. (1986), Mol. Cell. Biol. 6:955-958.
Yokota et al. (1986), The Lancet 765-766.
Akiyama et al. (1986), Science 232:1644-1646.
Bargmann et al. (1986), Nature 319:226-229.
Yamamoto et al. (1986), Nature 319:230-234.
Drebin et al. (1985), Cell, 41:695-706.

*Primary Examiner*—Robert A. Wax
*Assistant Examiner*—Stephanie W. Zitomer
*Attorney, Agent, or Firm*—Townsend and Townsend

[57] ABSTRACT

Amplification of the HER-2/neu oncogene is related to the status of neoplastic diseases, particularly breast and ovarian adenocarcinomas. The presence of multiple gene copies in tumor cells indicates that the disease is more likely to spread beyond the primary tumor site, and that the disease therefore may require more aggressive treatment than might otherwise be indicated by other diagnostic factors. In particular, the degree of gene amplification appears to provide greater prognostic utility than either the estrogen receptor or the progesterone receptor, and provides utility equal to that of the determination of lymph node status. The information provided by the gene amplification test, however, is not duplicative with the determination of lymph node status and the two tests together provide greatly improved prognostic utility.

22 Claims, No Drawings

DETERMINATION OF STATUS IN NEOPLASTIC DISEASE

BACKGROUND OF THE INVENTION

1. Field of the Invention

The present invention relates generally to monitoring the status of neoplastic diseases. More particularly, it relates to a method for determining likelihood of patient survival and time to relapse for neoplastic diseases, particularly breast and ovarian adenocarcinomas.

The ability to monitor neoplastic disease status can be of great value. In addition to improving prognostication, knowledge of the disease status allows the attending physician to select the most appropriate therapy for the individual patient. For example, patients with a high likelihood of relapse can be treated rigorously, usually involving systemic chemotherapy and/or radiation therapy. When there is a lesser likelihood of relapse, less aggressive therapies can be chosen. Because of the severe patient distress caused by the more aggressive therapy regimens, it would be desirable to distinguish with a high degree of certainty those patients requiring such aggressive therapies.

Unfortunately, no single factor or combination of factors in human breast cancer is completely reliable in assessing disease status. While the degree of tumor involvement in lymph nodes or distant sites (tissues) generally provides the best correlation with likelihood of survival and time to relapse, the determination can only be made after the disease has progressed to the point of such involvement. Other factors, such as primary tumor size, hormonal status of the tumor, and the like, provide additional information, but still fall short of providing the desired reliability and early detection capability.

In the case of breast adenocarcinomas, the decision for chemotherapy after surgical removal of the tumor is usually based on the number of lymph nodes affected. A determination of nodal status, however, is still insufficient to confidently predict the status of the disease.

It would therefore be desirable to provide alternative factors which can be measured in order to determine the status of neoplastic diseases in human patients, particularly breast and ovarian adenocarcinomas. It would be further desirable if such factors provided a high correlation with disease status and allowed for determination of status at an early stage in the disease.

2. Description of the Background Art

A human proto-oncogene appearing to have tyrosine kinase activity was independently identified by three research groups: Semba et al. (1985) Proc. Natl. Acad. Sci. USA 82:6497-6501 (designating the gene c-erbB-2); Coussens et al. (1985) Science 230:1132-1139 (designating the gene HER2); and King et al. (1985) Science 229:974-976. Hereinafter, this gene is referred to as HER-2/neu. A related rat gene (designated neu) was reported in Schecter et al. (1985) Science 229:976-978. Amplification of the gene and/or increased translation of expression of the gene have been observed in tumor cells and cell lines. See, e.g., Fukushige et al. (1986) Mol. Cell. Biol. 6:955-958 where amplification and elevated expression (mRNA) of the gene was observed in the MKN-7 gastric cancer cell line; Coussens et al. (1985) supra., where elevated transcription of the gene was observed in cell lines from a hepatoblastoma, a Ewing sarcoma, a rhabdomyosarcoma, two neuroblastomas, and a Wilms tumor; and King et al. (1985) supra., where amplification of the gene was observed in a mammary carcinoma cell line. Yokota et al. (1986) Lancet I:765-767 disclose amplification of the HER-2/neu gene observed in breast, kidney, and stomach adenocarcinomas. Akiyama et al. (1986) Science 232:1644-1646 discloses the preparation of antibodies against a synthetic 14 amino acid fragment of the HER-2/neu gene product. The antibodies were used to isolate and characterize the gene product as it is expressed in MKN-7 adenocarcinoma cells.

SUMMARY OF THE INVENTION

The survival of a patient with a neoplastic disease, such as a breast or ovarian adenocarcinoma, can be determined by screening a patient sample for amplification of the HER-2/neu gene. Gene amplification has been found to correlate with both a decreased chance of long term survival as well as a shortened time to relapse of the disease. Patients displaying such gene amplification, even at relatively early stages of the disease, may be treated more rigorously in order to increase their chances for survival.

Gene amplification is defined to be at least two or more copies of the HER-2/neu gene, often being five or more copies of the gene, and frequently being as many as twenty or more copies of the gene. Gene amplification and/or expression may be measured in the patient sample either directly, for example, by Southern blotting (DNA analysis) using an appropriate probe, such as pCER 204, pMAC117, or λ107. Gene expression, alternatively, may be measured either by Northern blotting to quantitate the transcription of mRNA, or by immunological methods, such as immunohistochemical staining of tissue sections and assay of body fluids, to directly quantitate the expression of gene product.

DESCRIPTION OF THE SPECIFIC EMBODIMENTS

The HER-2/neu gene was independently isolated by several research groups and has been designated in various ways, including c-erbB-2 (Semba et al. (1985) supra.), HER-2 (Coussens et al. (1985) supra.), and MAC117 (King et al. (1985) supra.). The HER-2/neu gene encodes an approximately 185 kilodalton (kd) glycoprotein which appears to possess tyrosine kinase activity and is closely related to but distinct from the epidermal growth factor receptor (EGFR) gene. HER-2/neu is found on band q21 of chromosome 17 of the human genome and generates messenger RNA (mRNA) transcripts which are 4.8 kilobases (kb) in length. The nucleotide sequence of the gene suggests that the resulting protein may have an extracellular domain, a transmembrane domain that includes two cysteine-rich repeat clusters, and an intracellular kinase domain, indicating that it may be a cellular receptor for a ligand.

The present invention depends on the detection of amplification of the HER-2/neu gene as a measure of patient disease status and survivability. In particular, such gene amplification is directly related to the invasiveness of the disease and likelihood that the tumor has or will metastasize. Thus, patients who test positively for HER-2/neu gene amplification are less likely to survive and will usually suffer a shorter time to relapse after surgical removal of the tumor than patients without such amplification. Thus, the patients displaying gene amplification may benefit from aggressive treatment regimens after surgical removal of their tumors.

Conversely, patients who do not display gene amplification may be less likely to require such rigorous treatment.

The present invention is useful for screening a wide variety of neoplastic diseases, including both solid tumors and hemopoietic cancers. Exemplary neoplastic diseases include carcinomas, such as adenocarcinomas and melanomas; mesodermal tumors, such as neuroblastomas and retinoblastomas; sarcomas, such as osteosarcomas, Ewing's sarcoma, and various leukemias; and lymphomas. Of particular interest are adenocarcinomas of the breast, ovaries, colon, lung, stomach, and liver, more particularly of the breast and ovaries.

Depending on the nature of the cancer, an appropriate patient sample is obtained. In the case of solid tumors, a tissue sample from the surgically removed tumor will be obtained and prepared for testing by conventional techniques. In the case of lymphomas and leukemias, lymphocytes, leukemic cells, or lymph tissues will be obtained and appropriately prepared. Other patient samples, including urine, serum, sputum, cell extracts, etc. will also find use with particular tumors.

Once the patient tissue or cell sample is obtained, detection of gene amplification can be accomplished in a variety of ways. Conveniently, gene amplification may be measured directly by DNA analysis such as Southern blot or dot blot techniques. Such blotting techniques require the use of a labeled DNA probe, typically a radiolabelled probe specific for the HER-2/neu gene which is being measured. Suitable probes are described in the scientific literature; see for example, Semba et al. (1985) supra.; King et al. (1985), supra., and Coussens et al. (1985), supra. Probes may also be prepared synthetically based on the known nucleotide sequences of the HER-2/neu gene reported in the same references.

For Southern blotting, high molecular weight DNA is obtained from the cells of the patient sample by conventional methods. The DNA is then digested with one or more restriction enzymes, and the resulting fragments separated on an agarose gel by electrophoresis. The DNA fragments are then transferred to a nylon or cellulose nitrate filter by blotting, and the DNA fixed by baking. The filter is then exposed to a labeled complementary probe and the regions of hybridization detected, usually by autoradiography. Dot blotting is similar, except that the DNA fragments are not separated on the gel. The degree of gene amplification is then determined by dilutional analysis or densitometry scanning, as described in the Experimental section hereinafter.

Alternately, gene expression (which corresponds to gene amplification) may be measured based on the level of mRNA transcription and/or gene product. mRNA transcription can be measured by a variety of techniques, including Northern blotting (Thomas (1980) Proc. Natl. Acad. Sci. USA 77:5201–5205), dot blots, and in situ hybridization. A variety of methods for measuring expression of the gene product exist, including Western blotting and immunohistochemical staining. Western blots are run by spreading a protein sample on a gel, usually an SDS gel, blotting the gel with a cellulose nitrate filter, and probing the filters with labeled antibodies. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al. (1980) Am. J. Clin. Path. 75:734–738.

Gene amplification may also be determined indirectly by assay of a patient body fluid to detect the presence of elevated levels of the gene product. Suitable body fluids include serum, urine, and breast exudate, and a wide variety of useful immunoassays are described in the patent and scientific literature. See, for example, U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Antibodies useful for immunohistochemical staining and/or assay of body fluids may be either monoclonal or polyclonal. Conveniently, the antibodies may be prepared against a synthetic peptide based on the reported DNA sequences of the HER-2/neu gene. Such synthetic peptides may then be used as an immunogen in preparing antibodies by well-known techniques. Alternatively, the natural gene product and/or portions thereof may be isolated and used as the immunogen.

Desirably, measurement of gene amplification will be performed quantitatively so that the number of gene copies can be estimated. Status of the disease correlates directly with the number of gene copies present in the tumor cells, and patients displaying even two copies of the HER-2/neu gene copies are at a higher risk of relapse than patients not displaying gene amplification. Moreover, as the number of HER-2/neu gene copies increases, the invasiveness and likelihood of metastasis also appears to increase. Thus, the number of gene copies should be taken as an important factor in assessing the disease status along with the traditional factors, including lymph node status, estrogen receptor status, progesterone receptor status, and the like. With all this information available, the treating physician is best able to assess the disease status and recommend the best treatment strategy to benefit the patient.

The following examples are offered by way of illustration, not by way of limitation.

EXPERIMENTAL

Tissue samples from 189 breast malignancies were obtained from an ongoing breast cancer study. Information available on the majority of the specimens included size of the primary tumor, estrogen receptor status, progesterone receptor status, disease stage, and status of the regional lymph nodes.

Initially, tissue samples from 103 primary breast cancers were evaluated for alternations in the HER-2/neu gene. DNA from individual tumors was prepared as described in Maniatis et al., *Molecular Cloning: A Laboratory Manual*, pp. 282–285 (Cold Spring Harbor Laboratory, 1982), digested with EcoRI, and subjected to Southern blot analysis using a $^{32}$P-labeled HER-2/neu-1 probe, which is known to detect a 13 kb hybridizing band in human DNA (Coussens et al. (1985) Science 230:1132).

DNA was extracted from tissues and digested with EcoRI restriction endonuclease, as described (Maniatis et al., Molecular Cloning: A Laboratory Manual, pp. 282–285 (Cold Spring Harbor Laboratory), 1982). A total of 12 μg of EcoRI-digested DNA was loaded onto 0.8% agarose gels, electropheresed, and transferred onto nylon filter papers (Biodyne) (Maniatis et al., supra.). All filters were baked in a vacuum oven for three hours at 80° C., pre-hybridized in 5X SSC (1X SSC is 0.15M NaCl/0.015M sodium citrate, pH 7.0) containing 50% formamide, 10% dextran sulfate, 0.1% SDS, 1 mg/ml of denatured salmon sperm DNA, and 4X Denhardts (100X Denhardts being 2% BSA, 2% ficoll, and 2% polyvinyl pyrolidone) for twelve hours, then hybridized in the same solution containing $2 \times 10^6$ cpm/ml of nick-translated HER-2 probe (Schechter et al., (1984) Nature 312:5113) which had been labeled with $^{32}P$ to a specific activity of $1 \times 10^8$ cpm/µg DNA. Hybridizing occurred at 42° C. for 48 hours, followed by washing of filters in 2X SSC for twenty minutes at room temperature, followed by two successive washes of thirty minutes each in 2X SSC, 0.1% SDS at 65° C., followed by one wash of thirty minutes in 0.5X SSC, 0.1% SDS at 65° C. Filters were then exposed to XAR-5 X-ray film (Kodak, Rochester, N.Y.) for autoradiography.

Dilutional analysis was then performed to assess the degree of HER-2/neu gene amplification. DNA was diluted in water or buffer to various dilutions, such as 1:2, 1:5, 1:10, 1:20, 1:100, etc., and Southern analysis performed along side single copy DNA samples for comparison.

Of the 103 samples examined, nineteen (18%) showed evidence of HER-2/neu gene amplification. The degree of amplification in individual cases was determined by dilutional analysis, as well as soft laser densitometry scanning. To determine that the amount of DNA loaded in each lane was equivalent, all filters were washed and rehybridized with a $^{32}P$-labeled arginase gene probe. This probe identifies a 15 kb hybridizing band on EcoRI-digested human DNA, and was selected as a control because it more appropriately assesses the relative amount and transfer of high molecular weight species than a probe hybridizing with low molecular species which transfer more readily on Southern blotting. All lanes were shown to contain equivalent amounts of high molecular weight DNA. Individual tumors were assigned to groups containing single copy, two to five copies, five to twenty copies, and greater than twenty copies of the HER-2/neu gene. Assignment of tumors to the various groups was done in a blinded fashion, in that they were made without knowledge of disease parameters. Analysis of the data for correlation between gene amplification and a number of disease parameters was then performed.

One hundred and three tumors were evaluated in the initial survey. There was no correlation between gene amplification and estrogen receptor status, with 7/38 (18%) of patients with amplification having less than 3 femtomoles/mg protein, and 12/65 (18%) having more than 3 femtomoles (p value=0.99); no correlation with progesterone receptor status, with 9/51 (18%) having less than 5 femtomoles, and 10/52 (19%) having more than 5 femtomoles (p value =0.85); no correlation with size of tumor, with 2/15 (13%) of patients having tumors less than 2.5 cm. 7/41 (17%) having tumors 2.5–5 cm, and 5/22 (23%) having tumors more than 5 cm in size (p value =0.82); and no correlation with age at diagnosis, with 4/25 (26%) being less than 50 years old and 13/65 (20%) being more than 50 years old (p value =0.99)(Table 1).

When analysis was performed for correlation between HER-2/neu amplification and number of positive lymph nodes, however, a trend was noted. Gene amplification was found in 4 of 34 patients (11%) with no involved nodes, 2 of 20 patients (10%) with one to three involved nodes, and 8 of 25 patients (32%) with more than three involved nodes (p value =0.11). If these data were examined comparing 0-3 positive nodes versus greater than 3 positive nodes, the correlation with number of nodes became more significant (p value $\leq 0.03$)(Table 1). Thus, there was a significant increase in incidence of HER-2/neu gene amplification in patients with more than three axillary lymph nodes involved with disease. A multivariate regression analysis to correlate HER-2/neu amplification with various disease parameters identified the number of positive nodes as the only significant factor, either alone or in combination, to correlate with gene amplification.

TABLE I

Correlation of HER-2/neu Amplification. With Various Disease Parameters in 103 Breast Tumors

| | Single Copy | 2–5 copies | 5–20 copies | >20 copies | Total | P-value** |
|---|---|---|---|---|---|---|
| Estrogen Receptor Status | | | | | | |
| ER+ | 53 | 2 | 9 | 1 | 65 | p = 0.99 |
| ER− | 31 | 1 | 2 | 4 | 38 | |
| Progesterone Receptor Status | | | | | | |
| PgR+ | 42 | 2 | 6 | 2 | 52 | p = 0.85 |
| PgR− | 42 | 1 | 5 | 3 | 51 | |
| Tumor Size | | | | | | |
| <2.5 cm | 13 | 1 | 1 | 0 | 15 | p = 0.82 |
| 2.5–5 cm | 34 | 1 | 5 | 1 | 41 | |
| >5 cm | 17 | 1 | 2 | 2 | 22 | |
| UNK* | 20 | 0 | 3 | 2 | 25 | |
| Patient Age | | | | | | |
| <50 years | 21 | 1 | 2 | 1 | 25 | p = 0.83 |
| >50 years | 52 | 2 | 7 | 4 | 65 | |
| UNK* | 11 | 0 | 2 | 0 | 13 | |
| Number of Involved Nodes | | | | | | |
| 0 nodes | 30 | 0 | 3 | 1 | 34 | p = 0.11 |
| 1–3 nodes | 20 | 0 | 1 | 1 | 22 | p ≦ 0.05 |
| >3 nodes | 17 | 2 | 4 | 2 | 25 | for 0–3 |
| UNK* | 17 | 1 | 3 | 1 | 22 | vs >3 |
| Total | 84 | 3 | 11 | 5 | 103 | |

*UNK = unknown.
**P-values arrived at by combining 5-20 and >20, since there were so few samples in the >20 group. Statistical analyses for correlation of HER-2/neu amplification with various disease parameters were performed by the chi-square test.

Further study was conducted on 100 breast cancer tissue samples from patients with positive axillary lymph nodes. All of the information available for the first group of 103 patients was also available for these patients. In addition, relapse and survival information was available, since these cases had a median follow-up of 46 months (range 24–86 months). Of these 100 samples, 86 yielded sufficient DNA for study. Amplification of the HER-2/neu gene was measured as in the initial survey, and amplification was found in 34 of the 86 patients (40%). The parameters which were analysed for correlation to HER-2/neu amplification were, again, estrogen receptor status (positive versus negative), progesterone receptor status (positive versus negative), size of tumor (less than 2.5 cm versus 2.5–5 cm versus more than 5 cm), age at diagnosis (less than 50 versus more than 50), and number of axillary nodes positive for disease involvement (1–3 versus more than 3). For this larger sample of node-positive patients, several statistically significant or nearly significant correlations were observed. In agreement with the preliminary survey, there was a correlation between number of involved lymph nodes and HER-2/neu amplification (Table II). In addition, there was a significant correlation with estrogen receptor status and size of primary tumor (Table II). Together, these two surveys yielded data on 189 patients and correlation of HER-2/neu amplification with various disease parameters in the combined group is shown in Table III.

TABLE II

Correlation of HER-2/neu Amplification With Various Disease Parameters in 86 Breast Tumors From Node-Positive Patients

|  | Single Copy | 2–5 copies | 5–20 copies | >20 copies | Total | P-value** |
|---|---|---|---|---|---|---|
| Estrogen Receptor Status | | | | | | |
| ER+ | 38 | 21 | 5 | 1 | 65 | p = 0.05 |
| ER− | 14 | 2 | 4 | 1 | 21 | |
| Progesterone Receptor Status | | | | | | |
| PgR+ | 31 | 18 | 4 | 1 | 54 | p = 0.14 |
| PgR− | 21 | 5 | 5 | 1 | 32 | |
| Tumor Size | | | | | | |
| <2 cm | 18 | 8 | 3 | 0 | 29 | p = 0.09 |
| 2–5 cm | 28 | 12 | 2 | 1 | 43 | p = 0.02 for |
| UNK* | 6 | 3 | 4 | 1 | 14 | <5 vs >5 |
| Patient Age | | | | | | |
| <50 years | 16 | 12 | 6 | 1 | 35 | p = 0.06 |
| >50 years | 36 | 11 | 3 | 1 | 51 | |
| Number of Involved Nodes | | | | | | |
| 1–3 nodes | 31 | 7 | 5 | 0 | 43 | p = 0.06 |
| >3 nodes | 21 | 16 | 4 | 2 | 43 | |
| Total | 52 | 23 | 9 | 2 | 86 | |

*UNK = unknown.
**P-values arrived at by combining 5–20 and >20, since there were so few samples in the >20 group. Statistical analyses for correlation of HER-2/neu amplification with various disease parameters were performed by the chi-square test.

TABLE III

Correlation of HER-2/neu Amplification With Various Disease Parameters in Combined Surveys (189 Patients)

|  | Negative | 2–5 | 5–20 | >20 | Total | P-value** |
|---|---|---|---|---|---|---|
| Estrogen Receptor Status | | | | | | |
| ER+ | 91 | 23 | 14 | 2 | 130 | p = 0.05 |
| ER− | 45 | 3 | 6 | 5 | 59 | |
| Progesterone Receptor Status | | | | | | |
| PgR+ | 73 | 20 | 10 | 3 | 106 | p = 0.06 |
| PgR− | 63 | 6 | 10 | 4 | 83 | |
| Tumor Size | | | | | | |
| <2 cm | 31 | 9 | 4 | 0 | 44 | p = 0.19 |
| 2–5 cm | 62 | 13 | 7 | 2 | 84 | |
| >5 cm | 23 | 4 | 6 | 3 | 36 | |
| UNK* | 20 | 0 | 3 | 2 | 25 | |
| Patient Age | | | | | | |
| <50 years | 37 | 13 | 8 | 2 | 60 | p = 0.11 |
| >50 years | 88 | 13 | 10 | 5 | 116 | |
| UNK* | 11 | 0 | 2 | 0 | 13 | |
| Number of Involved Nodes | | | | | | |
| 0 nodes | 30 | 0 | 3 | 1 | 34 | p = 0.002 |
| 1–3 nodes | 51 | 7 | 6 | 1 | 65 | |
| >3 nodes | 38 | 18 | 8 | 4 | 68 | |
| UNK* | 17 | 1 | 2 | 1 | 22 | |

*UNK = unknown.
**P-values arrived at by combining 5–20 and >20, since there were so few samples in the >20 group. Statistical analyses for correlation of HER-2/neu amplification with various disease parameters were performed by the chi-square test.

While these correlations were of interest, the strong association between HER-2/neu amplification and nodal status (p value=0.002) indicated that information on amplification of this gene may correlate with disease behavior, i.e., recurrences and survival. To test this, univariate survival analyses were performed comparing amplification to relapse and survival in this group of patients. A strong and highly statistically significant correlation was found between gene amplification and both time to disease relapse (p value = <0.0001) and survival (p value=0.0011) (Table IV). Moreover, when compared to other parameters, amplification of HER-2/neu was found to be superior to all other prognostic factors, with the exception of the number of positive nodes (which it equaled) in predicting time to relapse and overall survival in human breast cancer (Table IV A).

TABLE IV A

Results of Univariate Survival Analyses In Node-Positive Patients[1] Comparing Disease-Free Survival (Relapse) and Overall Survival to Factors Listed

| Factor | P-value Survival | P-value Relapse |
|---|---|---|
| Number of positive nodes | 0.0001 | 0.0002 |
| HER-2 | 0.0011 | <0.0001 |
| Log (PgR) | 0.05 | 0.05 |
| Size of Tumor | 0.06 | 0.06 |
| Log (ER) | 0.15 | 0.10 |
| Age | 0.22 | 0.61 |

[1]Patient cohort for both Table IV A and IV B consisted of 86 patients with node-positive breast cancer who had a median follow-up of 47 months (range 24–86 months). Median time to recurrence in this group was 62 months. Median time to death was 69 months.

TABLE IV B

Results of Multivariate Survival Analyses[2] In Node-Positive Patients to Evaluate Predictive Value of Various Prognostic Factors in a Multivariate Manner

| SURVIVAL | Regression Coefficients (Standard Errors) | P-Value |
|---|---|---|
| Number of positive nodes | 0.0938 ± 0.0256 | p = 0.0003 |
| HER-2 | 0.0872 ± 0.0388 | p = 0.02 |
| Log (ER) | −0.5158 ± 0.2414 | p = 0.03 |
| RELAPSE | | |
| Number of positive nodes | 0.0849 ± 0.0266 | p = 0.001 |
| HER-2 | 0.1378 ± 0.0425 | p = 0.001 |

[2]Cox's partially non-parametric regression model was used to evaluate the predictive power of various combinations and interactions of prognostic factors in a multivariate manner.

To determine if amplification of HER-2/neu was an independent prognosticator of disease behavior, multivariate survival analyses were performed on the 86 node-positive cases, and again, amplification of the gene proved to be a strong prognostic factor (Table IV B). Rearrangement of the HER-2/neu gene was rare. Of the total 198 tumors evaluated, three showed evidence of rearrangement, and in two of the three cases, the rearrangement was identical. Also, two of the rearranged HER-2/neu loci were amplified. The incidence of HER-2/neu rearrangement as determined by EcoRI digestion was too small to allow statistical correlations.

To determine whether the phenomenon of amplification of HER-2/neu in breast cancer extended to related growth factor receptors, all filters were analysed with the EGFR probe (Ullrich et al. (1984) Nature 309:418). Amplification of the EGFR gene was found in 4/189 (2%) of the cases, and rearrangement of the EGFR gene was found in one of those four cases. The incidence of EGFR amplification and rearrangement was too small to allow statistical correlation. Comparison of HER-2/neu amplification (53/189 or 28%) with that of the EGFR gene reveals the incidence of the former to be fourteen times greater than that of the latter, indicating that the phenomenon of gene amplification is not a general one for a related tyrosine-kinase-specific receptor in human breast cancer.

Although the foregoing invention has been described in some detail by way of illustration and example for purposes of clarity of understanding, it will be obvious that certain changes and modifications may be practiced within the scope of the appended claims and that use of this invention can extend to the detection, monitoring, and prognosis of a wide variety of human malignancies.

What is claimed is:

1. A method for screening patients to determine disease status, said method comprising:
    measuring the level of amplification or expression of the HER-2/neu gene in a sample from a patient suffering from breast or ovarian adenocarcinoma; and
    classifying those patients having an increased level of amplification or expression of the HER-2/neu gene relative to a reference level characteristic of normal cells as being more likely to suffer disease relapse or having a decreased chance of survival.

2. A method as in claim 1, wherein gene amplification is measured directly by DNA analysis with a probe specific for the HER-2/neu gene.

3. A method as in claim 1, wherein gene expression is measured by determination of gene product.

4. A method as in claim 1, wherein gene expression is measured by determination of mRNA transcription.

5. A method as in claim 1, wherein the expression of the HER-2/neu gene is determined by measuring the amount of gene product using a liquid phase immunoassay.

6. A method as in claim 2, wherein the amplification of the HER-2/neu gene is determined indirectly by assay of a body fluid from a patient for increased levels of HER-2/neu expression.

7. A method for determining a prognosis in patients suffering from breast or ovarian adenocarcinoma, said method comprising:
    determining the number of copies of the HER-2/neu gene in cells from a sample from a patient suffering from breast or ovarian adenocarcinoma; and
    classifying patients having only a single copy of the HER-2/neu gene as being less likely to suffer disease relapse than those patients having two or more copies of the HER-2-neu gene.

8. A method as in claim 7, wherein patients having at least five copies of the HER-2/neu gene are classified as having an increased risk of metastasis compared to patients having fewer copies of the gene.

9. A method as in claim 7, wherein the number of copies of the HER-2/neu gene is determined directly by Southern or dot blotting.

10. A method as in claim 7, wherein the expression of the HER-2/neu gene is determined by measuring the amount of the HER-2/neu mRNA transcripts or gene product, said expression corresponding to gene amplification.

11. A method as in claim 10, wherein the expression of the HER-2/neu gene is determined by measuring the amount of gene product by histochemical staining with labeled antibody specific for the gene product.

12. A method as in claim 10, wherein the expression of the HER-2/neu gene is determined by measuring the amount of gene product using a liquid phase immunoassay.

13. A method as in claim 7, wherein patients having more than two copies of the HER-2/neu gene are classified as having an increased risk of disease relapse compared to patients having only two copies of the gene.

14. A method as in claim 7, wherein the number of copies of the HER-2/neu gene is determined prior to lymph node involvement.

15. A method as in claim 7, wherein the number of copies of the HER-2/neu gene is determined indirectly by assay of a body fluid from a patient suffering from breast or ovarian adenocarcinoma for increased levels of HER-2/neu gene expression.

16. A method as in claim 15, wherein the fluid from a patient suffering from breast or ovarian adenocarcinoma is selected from the group consisting of serum, urine, and breast exudate.

17. A method for determining the proper course of treatment for patients suffering from breast or ovarian adenocarcinoma, said method comprising:
    determining the number of copies of the HER-2/neu gene in cells from a sample from a patient suffering from breast or ovarian adenocarcinoma;
    identifying patients having at least two copies of the HER-2/neu gene in the cells, which patients may require treatment proper for patients having a lesser chance of survival or decreased time to relapse; and
    identifying patients having only a single copy of the HER-2/neu gene in the cells, which patients may require treatment proper for patients having a greater chance of survival and being less likely to suffer disease relapse.

18. A method as in claim 17, wherein the number of copies of the HER-2/neu gene is determined directly by Southern or dot blotting.

19. A method as in claim 17, wherein the expression of the HER-2/neu gene is determined by measuring the amount of HER-2/neu mRNA transcripts or gene product, said expression corresponding to gene amplification.

20. A method as in claim 17, further comprising identifying those patients having five or more copies of the HER-2/neu gene, which patients may require treatment proper for patients having a lesser chance of survival or decreased time to relapse due to metastatis.

21. A method as in claim 17, wherein the proper treatment includes systemic chemotherapy or radiation therapy.

22. A method as in claim 17, wherein the number of copies of the HER-2/neu gene is determined prior to lymph node involvement.

* * * * *

UNITED STATES PATENT AND TRADEMARK OFFICE
CERTIFICATE OF CORRECTION

PATENT NO. : 4,968,603
DATED : November 6, 1990
INVENTOR(S) : Dennis J. Slamon, William L. McGuire, and Axel Ullrich It is certified that error appears in the above-identified patent and that said Letters Patent is hereby corrected as shown below:

On the title page, left-hand column, after "[75] Inventors: Dennis J. Slamon, Woodland Hills, Calif.; William L. McGuire, San Antonio, Tex." please insert --Axel Ullrich, Hindenbergstr. 23, 755 Rastatt, Federal Republic of Germany.--

Signed and Sealed this

Twenty-first Day of April, 1992

*Attest:*

HARRY F. MANBECK, JR.

*Attesting Officer*     *Commissioner of Patents and Trademarks*